United States Patent
Morrissey

Patent Number: 5,953,772
Date of Patent: Sep. 21, 1999

[54] SINK STATION AND METHOD

[76] Inventor: Donald J. Morrissey, 7255 Juniper Dr., Colorado Springs, Colo. 80908

[21] Appl. No.: 08/991,954

[22] Filed: Dec. 16, 1997

[51] Int. Cl.$^6$ ........................................... E03C 1/12
[52] U.S. Cl. ........................................ 4/679; 4/680
[58] Field of Search ............................. 4/679, 680, 681, 4/665, 638, 683; 433/92, 229

[56] References Cited

U.S. PATENT DOCUMENTS

| | | | |
|---|---|---|---|
| 3,404,458 | 10/1968 | Weiss et al. | 32/22 |
| 3,553,840 | 1/1971 | Bordelon | 32/22 |
| 3,636,633 | 1/1972 | Fuller et al. | 4/293 |
| 3,691,634 | 9/1972 | Buchtel et al. | 32/22 |
| 3,842,448 | 10/1974 | Kahn et al. | 4/263 |
| 4,228,006 | 10/1980 | Hanna | 4/665 |
| 4,344,756 | 8/1982 | Folkenroth et al. | 433/92 |
| 5,106,493 | 4/1992 | McIntosh | 4/665 |
| 5,313,677 | 5/1994 | Coe | 4/683 |

Primary Examiner—David J. Walczak
Attorney, Agent, or Firm—Richard W. Hanes

[57] ABSTRACT

A sink station system and method for accumulating and holding fluids and solid sediments. The sink station system incorporates a drain pipe serving to draw fluid out of a dental sink. The fluid flows down the drain pipe and into a fluid trap. As the sink is used, fluid accumulates in the fluid trap. As fluid accumulates in the trap beyond a predetermined level, the fluid rises upward through a water level pipe into a water level chamber wherein a float sensor is disposed. As the water rises to a predetermined level within the water level chamber, the float sensor is activated. Upon activation of the float sensor, a discharge pump is activated and accumulated fluid is pumped out of the system through a discharge pipe. The water level chamber and drain pipe fluidly communicate by means of an air vent that allows air accumulating above the fluid rising in the water level chamber out of the system to atmosphere through the drain pipe and sink.

2 Claims, 1 Drawing Sheet

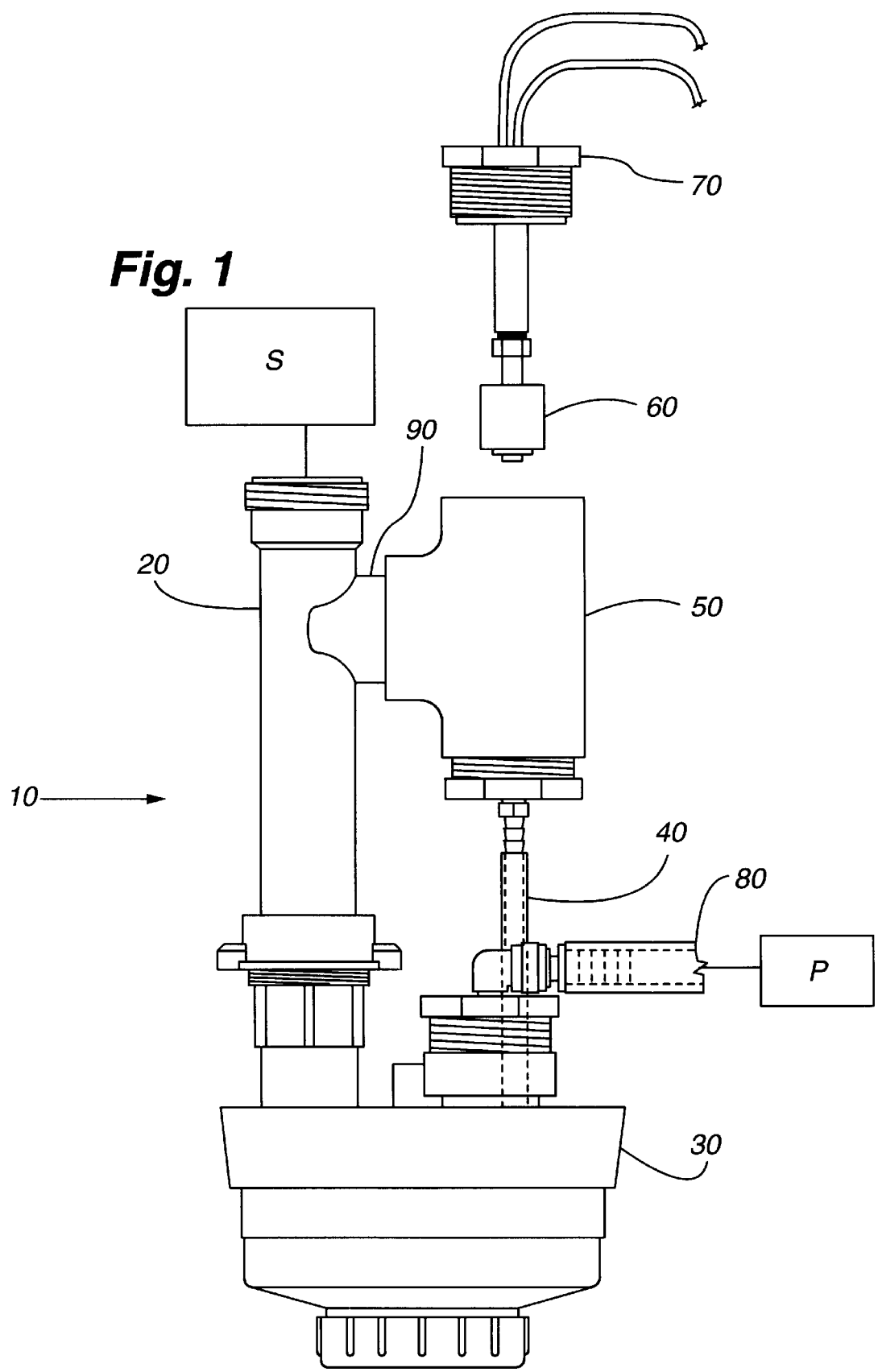

SINK STATION AND METHOD

FIELD OF INVENTION

The present invention relates to dental station accessories and, in particular, to an improved sink station and method that enables disposal of waste fluids by reverse gravity without the necessity of fixed plumbing.

BACKGROUND OF THE INVENTION

Heretofore, dental sink stations that have been utilized in disposal of fluid during a dental procedure have posed several problems for the dental practitioner. Among these problems are the alterations which must be made to the structure within which the sink is used. Another problem is the untimeliness involved in disposing of the fluid where a standard in-office reservoir is used.

Many dental sink stations utilize a fluid reservoir or variant thereof wherein the extracted fluid is collected during operation, thereby undermining optimal sanitary conditions. Such a fluid reservoir must periodically be emptied and, as a result, the system must be shut down at that time. Such a system can present a significant problem when the reservoir must be emptied while the dentist is performing a dental procedure on a patient. Other sink stations incorporate traditional gravity drains capable of disposing of the contents therein. However, such systems most often require a floor drain in close proximity which can be impractical or impossible to provide. Further, these systems do not allow collection of solid sediment for disposal as solid waste or convenient recovery of useful objects that may be inadvertently dropped down the drain.

Additionally, installation or removal of the aforementioned sink stations requires considerable plumbing and property improvements to access the required water and electricity. Such installations are typically fixed to a floor or wall and do not lend themselves to portability of the sink station that would allow accommodation of handicapped patients and better ergonomic efficiency during dental procedures. In such a case, the considerable inconvenience and expense incurred by the dental professional are obvious.

What is needed in the art is an improved dental sink station that accumulates fluid and sediments and then pumps the fluid out to an overhead plumbing system at such time as the quantity of waste demands. The station should also access any necessary water, electricity, and waste removal from overhead cables thereby permitting expeditious and convenient installation while minimizing or eliminating the need for altering the structure within which the receptacle is used. In addition, the station should be such that it can be easily moved thereby allowing accommodation of handicapped patients and better ergonomic efficiency during dental procedures.

The present invention accomplishes these objectives by providing a sink station system that accumulates and holds fluids and solid sediments. The sink station system incorporates a drain pipe serving to draw fluid out of a dental sink. The fluid flows down the drain pipe and into a fluid trap. As the sink is used, fluid accumulates in the fluid trap. As fluid accumulates in the trap beyond a predetermined level, the fluid rises upward through a water level pipe into a water level chamber wherein a float sensor is disposed. As the water rises to a predetermined level within the water level chamber, the float sensor is activated. Upon activation of the float sensor, a discharge pump is activated and accumulated fluid is pumped out of the system through a discharge pipe. The water level chamber and drain pipe fluidly communicate by means of an air vent that allows air accumulating above the fluid rising in the water level chamber out of the system to atmosphere through the drain pipe and sink, thereby preventing drain back-up through the sink. Water is prevented from entering the air vent by a deflector located at the junction of the drain pipe and sink.

Listed below are samples of patents based in part on dental sink devices. These patents are merely representative of the art and do not suggest the teachings of the present invention:

U.S. Pat. No. 3,404,458 (1968) to Weiss et al. discloses a portable dental unit requiring no external connections.

U.S. Pat. No. 3,553,840 (1971) to Bordelon discloses a mobile quick set-up orthodontic unit not requiring any external plumbing connections.

U.S. Pat. No. 3,636,633 (1972) to Fuller et al. discloses a dental console having a cabinet with a plurality of dental instruments mounted in the cabinet.

U.S. Pat. No. 3,691,634 (1972) to Buchtel et al. discloses a dental unit which may be located adjacent a dental chair, including a compact, floor mounted cabinet with a dental tray assembly pivotally mounted thereon by a conventional adjustable tray arm.

U.S. Pat. No. 3,842,448 (1974) to Kahn et al. discloses an apparatus for recycling a fluid for use in flushing a dental cuspidor.

U.S. Pat. No. 4,344,756 (1982) to Folkenroth et al. discloses a water recycling unit and system for dental operatories.

SUMMARY OF THE INVENTION

The primary aspect of the present invention is to provide an improved dental sink station system that accumulates fluid and solid sediments and then pumps the fluid out to an overhead plumbing system at such time as the quantity of waste demands.

Another aspect of the present invention is to provide an improved dental sink station system that accesses any necessary water, electricity, and waste removal from overhead cables thereby permitting expeditious and convenient installation while minimizing or eliminating the need for altering the structure within which the system is used.

Another aspect of the present invention is to provide an improved dental sink station system that can be easily moved thereby allowing accommodation of handicapped patients and better ergonomic efficiency during dental procedures.

Another aspect of the present invention is to provide a method of conveniently and automatically disposing of dental waste fluid while minimizing or eliminating the need for altering the structure within which the method is practiced.

Additional aspects, advantages and novel features of the invention will be set forth in part in the description which follows, and in part will become apparent to those skilled in the art upon examination of the following or may be learned by practice of the invention. The aspects and advantages of the invention may be realized and attained by means of the instrumentalities and combinations particularly pointed out in the appended claims.

The present invention provides a dental sink station system that accumulates add holds fluids and solid sediments. The sink station system incorporates a drain pipe serving to draw fluid out of a dental sink. The fluid flows down the drain pipe and into a fluid trap. As the sink is used, fluid accumulates in the fluid trap. As fluid accumulates in the trap beyond a predetermined level, the fluid rises upward through a water level pipe into a water level chamber wherein a float sensor is disposed. As the water rises to a predetermined level within the water level chamber, the float sensor is activated. Upon activation of the float sensor, a discharge pump is activated and accumulated fluid is pumped out of the system through a discharge pipe. The water level chamber and drain pipe fluidly communicate by means of an air vent that allows air accumulating above the fluid rising in the water level chamber out of the system to atmosphere through the drain pipe and sink, thereby preventing drain back-up through the sink. Water is prevented from entering the air vent by a deflector located at the junction of the drain pipe and sink.

BRIEF DESCRIPTION OF THE DRAWING

FIG. 1 is a partially exploded side view of the preferred embodiment of the improved dental sink station system.

Before explaining the disclosed embodiment of the present invention in detail, it is to be understood that the invention is not limited in its application to the details of the particular arrangement shown, since the invention is capable of other embodiments. Also, the terminology used herein is for the purpose of description and not of limitation.

DESCRIPTION OF THE PREFERRED EMBODIMENT

Referring to FIG. 1 a sink station system 10 incorporates a drain pipe 20 serving to draw fluid out of a dental sink S. The fluid flows down the drain pipe 20 and into a fluid trap 30. As the sink is used, fluid accumulates in the fluid trap 30. As fluid accumulates in the trap 30 beyond a predetermined level, the fluid rises upward through water level pipe 40 (partially hidden) into a water level chamber 50 wherein a float sensor 60 is disposed. As the water rises to a predetermined level within the water level chamber 50, the float sensor 60 is activated. Upon activation of the float sensor 60, an electrical signal flows through a sensor switch assembly 70 causing activation of a discharge pump P that pumps accumulated fluid out of the system through a discharge pipe 80. The water level chamber, 50 and drain pipe 20 fluidly communicate by means of an air vent 90 that allows air accumulating above the fluid rising in the water level chamber 50 out of the system to atmosphere through the drain pipe 20 and sink.

Although the present invention has been described with reference to preferred embodiments, numerous modifications and variations can be made and still the result will come within the scope of the invention. No limitation with respect to the specific embodiments disclosed herein is intended or should be inferred.

I claim:

1. An improved method of fluid waste disposal comprising the steps of:

a) providing a sink station system comprising:
      a drain pipe;
      a fluid trap disposed below the said drain pipe;
      a vertically oriented water level pipe having upper and lower ends where the lower end thereof is disposed in the fluid trap;
      a water level chamber connected to the upper end of the water level pipe;
      a float sensor disposed within said water level chamber;
      a discharge pipe in fluid communication with said fluid trap; and an air vent in fluid communication with said drain pipe and said water level pipe;

b) attaching a sink to said drain pipe; and c) introducing fluid waste into the sink, thereby allowing the fluid waste to enter said drain pipe;

whereby upon accumulation of fluid waste to a predetermined level within said water level chamber, said float sensor activates a discharge pump external to said sink station system, thereby drawing the fluid waste through said discharge pipe and out of said sink station system.

2. Apparatus for removing waste fluid from a basin having a gravitational bottom drain, comprising, vertically oriented drain pipe means having a first end for connection to the bottom drain of the basin and an open second end, a fluid collection bowl disposed below the open second end of the drain pipe means, a vertically oriented water level pipe positioned in parallel with the drain pipe means and having top and bottom ends, wherein the bottom end is disposed within the fluid collection bowl, a water level chamber having bottom and sides, and including means interconnecting the bottom of the chamber to the top end of the water level pipe for conducting fluid from the water level pipe into the chamber, a float sensor disposed within the chamber, electrical switch means responsive to the vertical position of the float sensor, and fluid discharge means disposed within the fluid collection bowl.

* * * * *